United States Patent
Harrison et al.

(10) Patent No.: US 9,058,649 B2
(45) Date of Patent: Jun. 16, 2015

(54) ULTRASOUND IMAGING SYSTEM AND METHOD WITH PEAK INTENSITY DETECTION

(75) Inventors: Gerard Joseph Harrison, Snohomish, WA (US); Thomas Patrice Jean Arsene Gauthier, Seattle, WA (US)

(73) Assignee: Koninklijke Philips N.V., Eindhoven (NL)

( * ) Notice: Subject to any disclaimer, the term of this patent is extended or adjusted under 35 U.S.C. 154(b) by 56 days.

(21) Appl. No.: 13/885,406

(22) PCT Filed: Dec. 7, 2011

(86) PCT No.: PCT/IB2011/055513
§ 371 (c)(1),
(2), (4) Date: May 15, 2013

(87) PCT Pub. No.: WO2012/080905
PCT Pub. Date: Jun. 21, 2012

(65) Prior Publication Data
US 2013/0251221 A1 Sep. 26, 2013

Related U.S. Application Data (60) Provisional application No. 61/422,764, filed on Dec. 14, 2010.

(51) Int. Cl.
| | |
|---|---|
| *G06K 9/00* | (2006.01) |
| *G06T 7/00* | (2006.01) |
| *A61B 8/08* | (2006.01) |
| *A61B 8/00* | (2006.01) |

(52) U.S. Cl.
CPC ............... *G06T 7/0012* (2013.01); *A61B 8/467* (2013.01); *A61B 8/469* (2013.01); *A61B 8/481* (2013.01); *A61B 8/54* (2013.01); *A61B 8/58* (2013.01)

(58) Field of Classification Search
CPC .................. G06T 7/0012; G06T 2207/10132; G06T 2207/10136; A61B 8/46; A61B 8/481; A61B 8/467; A61B 8/469; A61B 8/54; A61B 8/58
See application file for complete search history.

(56) References Cited

U.S. PATENT DOCUMENTS 3,798,366 A * 3/1974 Hunt et al. ..................... 374/124
3,909,521 A * 9/1975 Hunt et al. ..................... 348/167

(Continued)

OTHER PUBLICATIONS

Li et al: "Time-Intesity-Based Quantification of Vascularity With Single-Level Dynamic Contrast-Enhanced Ultrasonography"; Journal of Ultrasound Medicine, 2005, 24:975-983.

(Continued)

*Primary Examiner* — Manav Seth (57) ABSTRACT

The present invention relates to an ultrasound imaging system (10) and method that allow for a quantitative analysis of the acquired images during acquisition and for an optimized workflow for image acquisition and analysis. The proposed ultrasound imaging system (10) comprises a transducer (12) configured to acquire ultrasound images (14) of an object based on one or more adjustable acquisition parameters, an analyzer (22) configured to analyze an ultrasound image (14) in real-time for a mean intensity value (24), and a processor (28) configured to determine in real-time when the mean intensity value (24) has reached a peak and to change the setting of at least one of the one or more adjustable acquisition parameters after a peak has been determined.

10 Claims, 4 Drawing Sheets

(56) References Cited

U.S. PATENT DOCUMENTS

| | | | |
|---|---|---|---|
| 4,504,908 A * | 3/1985 | Riederer et al. | 600/431 |
| 4,888,795 A * | 12/1989 | Ando et al. | 348/14.14 |
| 5,119,195 A * | 6/1992 | Christopher | 348/623 |
| 5,224,141 A * | 6/1993 | Yassa et al. | 378/98.2 |
| 5,313,948 A * | 5/1994 | Murashita et al. | 600/448 |
| 5,743,266 A | 4/1998 | Levene et al. | |
| 6,385,332 B1 | 5/2002 | Zahalka et al. | |
| 7,596,277 B2 * | 9/2009 | Govindaswamy et al. | 382/232 |
| 7,727,154 B2 * | 6/2010 | Kato et al. | 600/458 |
| 2006/0173311 A1 | 8/2006 | Hao et al. | |
| 2007/0083120 A1 * | 4/2007 | Cain et al. | 600/439 |
| 2007/0139449 A1 * | 6/2007 | Bergquist et al. | 345/691 |
| 2007/0178047 A1 * | 8/2007 | Kawabata | 424/9.5 |
| 2008/0037867 A1 * | 2/2008 | Lee et al. | 382/168 |
| 2008/0319356 A1 * | 12/2008 | Cain et al. | 601/2 |
| 2009/0112097 A1 | 4/2009 | Kato et al. | |
| 2009/0244113 A1 * | 10/2009 | Bergquist et al. | 345/691 |
| 2010/0094133 A1 | 4/2010 | Yoshiara et al. | |
| 2011/0279709 A1 * | 11/2011 | Nonaka et al. | 348/231.6 |

OTHER PUBLICATIONS

Lucidarme et al: "Blood Flow Quantification With Contrast-Enhanced US: "Entrance in the Section" Phenomenon-Phantom and Rabbit Study"; Radiology, 2003, pp. 473-479.

Levienaise-Obadia et al: "Adaptive Segmentation of Ultrasound Images" Image and Vision Computing 17 (1999) 583-588.

* cited by examiner

ULTRASOUND IMAGING SYSTEM AND METHOD WITH PEAK INTENSITY DETECTION

FIELD OF THE INVENTION

The present invention relates to a system and method for acquiring and analyzing ultrasound images. The invention also relates to a computer program for implementing said method.

BACKGROUND OF THE INVENTION

The advantages of ultrasound include the real time imaging capability, low cost, flexibility in its application, and the fact that no ionizing radiation is used. However, non-enhanced ultrasound, including the commonly used gray-scale ultrasound imaging, may not be able to visualize a particular target (e.g., a tumor) with the desired contrast, and in some cases, may not visualize the target at all.

Contrast-enhanced ultrasound (CEUS) can provide superior visualization of tumors, vascularity, and other tissues of interest compared to non-contrast enhanced ultrasound imaging. However, the contrast enhancement after injection of the contrast agent is a transient phenomenon. After injection, there is typically a first phase where the concentration of contrast agent in the target area increases. This phase is called wash-in time. The concentration of the contrast agent (which corresponds to the intensities in the contrast-enhanced images) increases until a peak is reached. The time between injection and peak is called time-to-peak. Subsequently, the contrast agent is washed out and the intensity in the contrast-enhanced images decreases again. This dynamic behavior yields a characteristic time intensity curve.

Current work flow is typically such that the ultrasound images are first acquired, then transferred to a work station and finally quantitatively analyzed on the work station. The analysis of the images thus occurs after the acquisition of the images. Typical file sizes from contrast enhanced ultrasound acquisition are on the order of several MB. A typical study is made up of many files, which can result in several GB of overall data.

U.S. Pat. No. 5,743,266 discloses a method for producing real-time colorized, contrast enhanced images from a sequence of grey-scale video images obtained during diagnostic ultrasound. The particular colorizing scheme varies according to which information parameter is desired to be displayed in real-time.

SUMMARY OF THE INVENTION

It is an object of the present invention to provide an ultrasound imaging system and method that allow for a quantitative analysis of the acquired images during acquisition.

It is a further object of the present invention to allow for an optimized workflow for image acquisition and analysis.

In a first aspect of the present invention an ultrasound imaging system is presented that comprises:
a transducer configured to acquire ultrasound images of an object based on one or more adjustable acquisition parameters,
an analyzer configured to analyze an ultrasound image in real-time for a mean intensity value, and
a processor configured to determine in real-time when the mean intensity value has reached a peak and to change at least one of the one or more adjustable acquisition parameters after a peak has been determined.

In a further aspect of the present invention a method for acquiring and analyzing ultrasound images is presented that comprises
acquiring ultrasound images of an object based on one or more acquisition parameters,
analyzing an ultrasound image in real-time for a mean intensity value,
determining when the mean intensity value has reached a peak, and
changing at least one of the one or more acquisition parameters after a peak has been determined.

According to a further aspect of the present invention, a computer program is presented that comprises program code means for causing a computer, when said computer program is carried out on the computer, to carry out the steps of:
analyzing an ultrasound image in real-time for a mean intensity value, said ultrasound image being one of a plurality of ultrasound images of an object acquired based on one or more acquisition parameters,
determining when the mean intensity value has reached a peak, and
changing at least one of the one or more acquisition parameters after a peak has been determined.

Preferred embodiments of the invention are defined in the dependent claims. It shall be understood that the claimed method has similar and/or identical preferred embodiments as the claimed device and as defined in the dependent claims.

Different to the currently known devices of this art, according to the present invention the acquisition of ultrasound images is not independent of the acquired images, but instead it is adapted at the intensities that are measured. The basic quantitative analysis of the images (performed by determining a mean intensity value) is done in real-time, which allows adapting parameters of the acquisition during the acquisition procedure. For example, the spatial and temporal accuracy of the acquired ultrasound images can be increased shortly before the peak intensity frame, and reduced after the peak intensity has been determined.

Because the ultrasound images are acquired at subsequent time points, they are sometimes also referred to as frames of an ultrasound video. In the following, the terms image and frame can refer to 2D images or 3D image volumes.

Real-time typically means that the processing is so quick, e.g. only several ms, that the user does not notice any delay. In the context of this application it can also refer to processing that is finished while image acquisition is still ongoing, for example a computation of some quantitative measure could take one or more seconds and still be considered as real-time in the context of this invention.

In a preferred embodiment, the processor is configured to compare the mean intensity value of a current image with the mean intensity values of one or more previous images for determining when the mean intensity value has reached a peak. There are different ways how such a comparison can be implemented. For example, a moving average can be computed and the peak is determined based on the derivative of this moving average.

In another embodiment, the ultrasound imaging system further comprises a notification unit, in particular an LED, a display, or a loudspeaker 30, wherein the processor is configured to control the notification unit to notify a user when it has determined that the mean intensity value has reached a peak. Notifying the user about the detection of the peak allows the user, e.g. a physician, to react accordingly. For example, if the peak is determined unusually early or late after administration of a contrast agent, the physician might want to perform additional exams and it can be helpful if he is acoustically notified of the peak detection result (in addition to displaying the peak time on a display).

The present invention is not limited to be used only in situations where a contrast agent is applied. The ultrasound imaging system of the present invention can also be used when a user is searching for an ultrasound reflector that yields a bright spot on the acquired ultrasound image. For example, microcalcifications in the breast (which may be an indication of a precancerous condition) can result in increased intensity on the ultrasound image. While the user moves the transducer over the breast, the system can automatically detect when the mean pixel intensity in the region of interest has a peak and convey to the user that the likelihood of finding a microcalcification near the current location of the transducer is particularly high. For example, the system may emit a sound or display a message to the user to let her know that she should focus her attention on that particular image or that particular area where the current image was acquired. At the same time, the processor could adapt the image acquisition, e.g. acquire images with higher quality near the suspected location of the microcalcification.

This further simplifies the examination procedure and makes the presented ultrasound imaging system also useful for users who are not physicians. For example, women could even use the ultrasound imaging system according to the present invention for self-examination. Once the system has detected a peak in the mean intensity value, the images could be acquired with an increased storage frame rate and these stored images could then be reviewed by an experienced physician.

In another preferred embodiment, the ultrasound imaging system further comprises a storage configured to store the ultrasound images, wherein the adjustable acquisition parameters include a storage frame rate at which the transducer stores ultrasound images in the storage. Thus, the processor can modify the storage frame rate after a peak in the intensity has been determined. The inventors realized that reducing the size of the acquired ultrasound images by dynamically adjusting the storage frame rate is a key to improving clinical workflow because the transfer of the files (which are typically several GB in total file size) can be a severe bottleneck.

In another embodiment, the processor is configured to reduce the storage frame rate after it has determined that the mean intensity value has reached a peak. This is useful for example when a contrast agent was administered to an object in the field of view of the transducer. In the case of contrast-enhanced ultrasound (CEUS), the patient's volume of interest is supposed to contain a contrast agent. Prior to the diagnostic imaging of, for example, a tumor, the contrast agent is brought to the volume of interest, e.g. by means of a liquid contrast agent which is injected into the body of the patient (object) or otherwise administered, e.g. orally, to the patient.

Generally, various ways for bringing the contrast agent into the field of view exist. In particular, in case of a patient into whose body the contrast agent is to be introduced, the contrast agent can be introduced by surgical and non-surgical methods, and there are both methods which require an expert (such as a medical practitioner) and methods which do not require an expert, which can, e.g., be carried out by laypersons or persons of ordinary skill or the patient himself/herself. Among the surgical methods, there are potentially non-risky and/or safe routine interventions, e.g. involving an invasive step such as an inject of contrast agent into a blood vessel (if such an injection is at all to be considered a surgical method), i.e. interventions which do not require considerable professional medical expertise to be carried out and which do not involve serious health risks. Further, non-surgical methods like swallowing or inhalation can be applied.

Generally, the contrast agents are pre-delivered or pre-administered before the data acquisition is started. In embodiments, it is, however, also possible that further contrast agent is delivered/administered into the field of view.

Particularly in the case where contrast agent is administered only before the acquisition is started, the concentration of contrast agent in the volume of interest will increase up to a peak and then decrease, during the so called wash-out period. Once the concentration of contrast agent in the target volume has decreased too much due to wash-out, the CEUS image intensities decrease accordingly and the images are less important for diagnosis. After the peak intensity has been reached, the wash-out phase begins and the mean intensity in the images is decreasing. The details of the time-intensity curve after the peak intensity are less important for diagnosis. Hence, reducing the rate at which ultrasound image frames are stored after the peak intensity frame allows reducing the required storage size of the images while still acquiring a complete time-intensity curve that also includes the wash-out region. Because the area around the peak intensity is also relevant for diagnosis and because, due to noise in the acquisition process, the image that corresponds to the peak intensity is possibly not precisely identified, the storage frame rate is preferably only reduced a predetermined time after the peak of the mean intensities has been detected.

In another embodiment, the processor is configured to continuously reduce the storage frame rate after it has determined that the mean intensity value has reached a peak. Reducing the storage rate continuously corresponds better to the continuously decreasing expected importance of the acquired intensities.

In another embodiment, the processor is configured to control the transducer to stop acquiring ultrasound images a predetermined time after it has determined that the mean intensity has reached a peak. This also contributes to reducing the file size. If it is known that an almost complete wash-out of contrast agent from an organ is expected, e.g. 90 s after the peak, a longer acquisition of ultrasound images only increases the overall file size but does not contribute to improved diagnosis.

In another embodiment, the ultrasound imaging system further comprises a first user interface for identifying the object as one of several objects, wherein the predetermined time depends on the selected object. These several objects can for example be a pre-determined selection of organs. If specific properties of these organs are known (for example the expected wash-out time or a preferred location of the transmit focus, or a preferred number of focal zones), these parameters can automatically be set accordingly.

In yet another embodiment, the mean intensity value is the mean intensity of a region of interest within the ultrasound images. Usually, the acquired ultrasound images do not only show the object or organ of interest, but also other structures, where the intensities might also be varying over time. It is thus beneficial to delineate a region of interest which only includes the object or organ of interest and to determine the peak based only on the mean intensity values that are determined for this region of interest.

In a preferred embodiment, the ultrasound imaging system further comprises a second user interface, wherein the second user interface is adapted for allowing a user to define the region of interest within the ultrasound images. For example, the second user interface could be a touch screen, which allows a physician to quickly indicate the outline of an organ.

In another embodiment, the ultrasound imaging system further comprises a region identification unit configured to automatically define a region of interest within the ultrasound images. Determining the region of interest automatically, e.g. based on the organ selection that the user indicated through the first user interface, can further accelerate the clinical workflow. Different techniques are known for automatically identifying organs in ultrasound images, for example U.S. Pat. No. 6,385,332 discloses an automated ultrasound segmentation method comprising the steps of automated initial contour identification, followed by application of a geometrically deformable model (GDM). Even though fully automatic segmentation would be ideal, this is currently not always feasible given the quality of ultrasound images. Levienaise-Obadia and Gee ("Adaptive segmentation of ultrasound images", Image and Vision Computing, Volume 17, Issue 8, June 1999, Pages 583-588) disclosed a method that allows a semi-automatic approach where statistical models are trained on-the-fly by observing boundaries accepted by the user. In this way, user intervention in a particular slice is sensibly exploited to reduce the need for intervention in subsequent slices.

In yet another embodiment, the analyzer is configured to analyze the ultrasound image for a time to peak, a transit time, a wash-in time and/or a wash-out time.

In yet another embodiment, the ultrasound imaging system further comprises a display, wherein the mean intensity value, the time to peak, the transit time, the wash-in time and/or the wash-out time are displayed in real-time on the display.

Evaluating and displaying these additional quantitative measures during the image acquisition accelerates clinical workflow because it is not necessary to first transfer the acquired images for offline evaluation. Ideally, all required quantitative analysis is performed in real-time on the device, such that no time-consuming post-acquisition analysis is necessary.

BRIEF DESCRIPTION OF THE DRAWINGS

These and other aspects of the invention will be apparent from and elucidated with reference to the embodiment(s) described hereinafter. In the following drawings

DETAILED DESCRIPTION OF THE INVENTION

Figure 1:
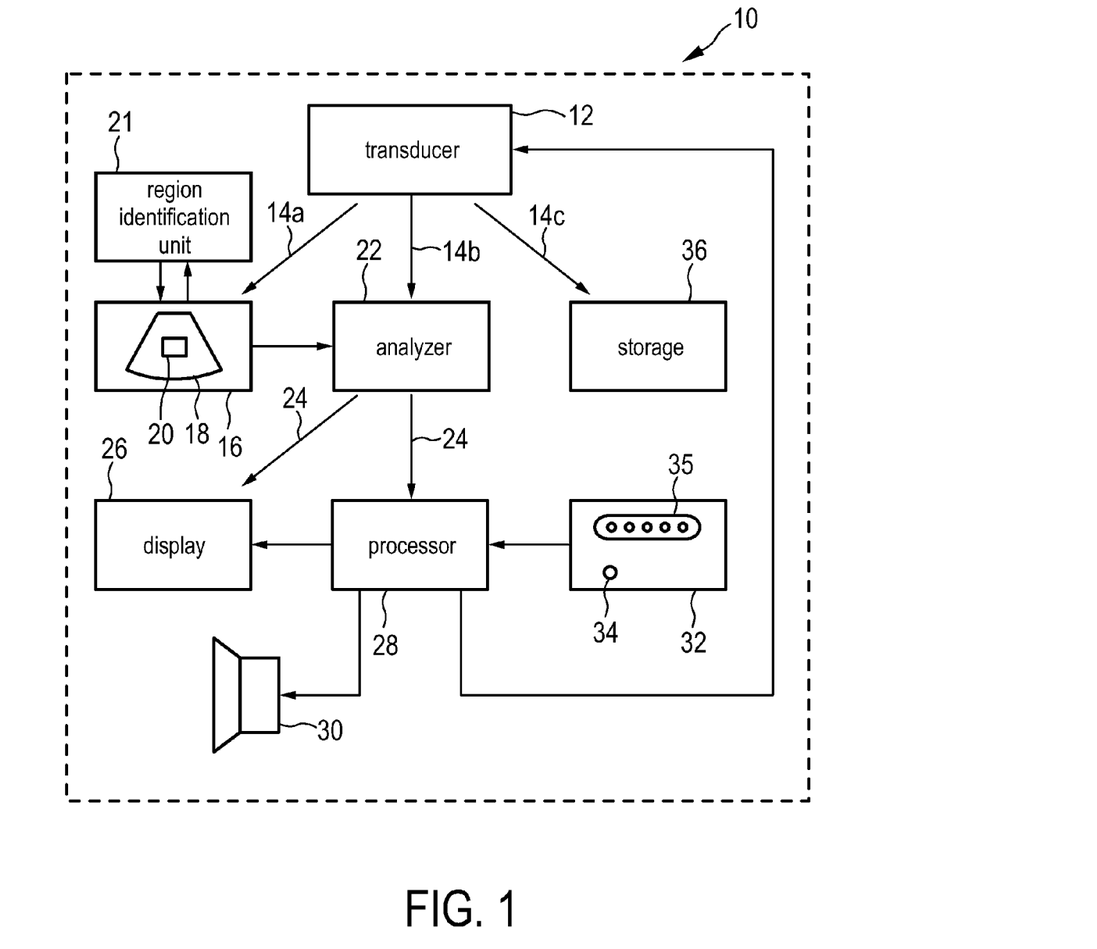
FIG. 1 is a block diagram of one embodiment of an ultrasound imaging system in accordance with the present invention.
Figure 2:
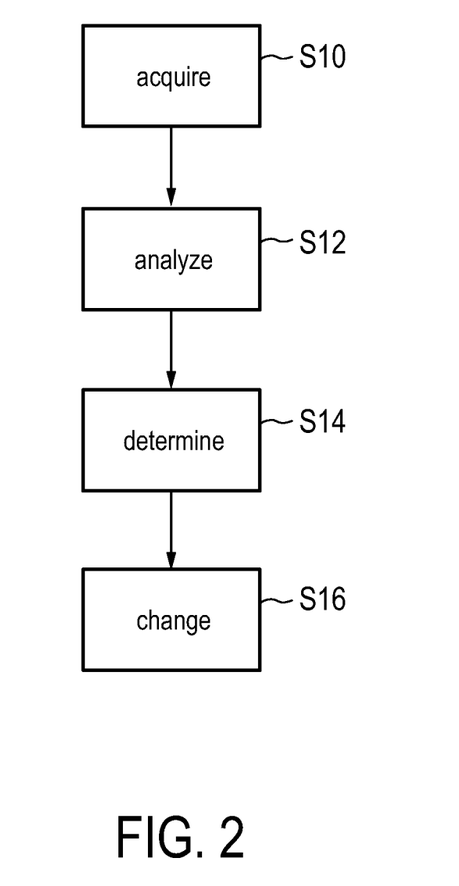
FIG. 2 is a flow chart of a method according to the present invention.

FIG. 1 is a block diagram of one embodiment of an ultrasound imaging system 10 in accordance with the present invention; FIG. 2 is a flow chart of a corresponding method. A transducer 12 acquires (S10) ultrasound images 14 from an object. The ultrasound images 14 are sent to a first user interface 16, which in this embodiment also comprises a display 18 for showing the ultrasound images 14. The first user interface 16 is adapted to allow a user to define a region of interest 20 in the images 14. For example, the first user interface 16 could comprise a touch screen, where the user could identify the region of interest 20 by pointing at the target area. To enable the user to accurately define the region of interest 20, the system 10 preferably first acquires and displays at least one ultrasound image 14, such that the user can identify the region 20 within this image 14. Alternatively, the region identification unit 21 can be used to automatically determine a region of interest 20. For example, the region identification unit 21 can comprise a first user interface which lets the user select an object from a selection of objects, e.g. different organs. The region identification unit 21 could then use template images or reference points of these organs in order to identify the organs within the ultrasound images 14. The automatically identified region of interest 20 can be shown to the user on display 18. The user can verify that the region 20 is placed correctly, e.g. by pushing an OK button, and the region 20 is subsequently used for determining a mean intensity value 24 within this region 20.

The transducer 12 also sends ultrasound images 14b to an analyzer 22. The analyzer 22 analyzes (S12) the defined region 20 of the ultrasound images 14b for mean intensity values 24. The mean intensity values 24 and further quantitative characteristics of the time intensity curve such as the rise time and the area under the curve can be shown in real-time on a display 26. This has the advantage that the user can obtain quantitative values of the region of interest 20 while he is performing the exam. The mean intensity values 24 are processed by a processor 28 in order to determine in real time when the mean intensity value 24 has reached a peak 38. It should be noted that ultrasound images 14 are noisy and hence also the mean intensity values 24 are assumed to be noisy. Therefore, as will be described below, different algorithms can be used in order to identify a true peak 38 of the mean intensity values 24, which is not just a local outlier.

Once the processor 28 has determined that a peak 38 has occurred it controls the display 26 to show that the peak 38 has been detected. The detection of the peak 38 is performed by comparing the mean intensity values 24 of recently acquired images 14 with the mean intensity values 24 of previously acquired images 14. For example, it could compare the average mean intensity I3 of the last three acquired images with the average of the mean intensity I12 of the last 12 acquired images and the average of the mean intensity I6 of the last six acquired images and determine (S14) a peak if I6 is significantly higher than I12 and I3.

According to another embodiment of a method according to the present invention the slope changes are tracked over time. The change in mean echo intensity of the region of interest, from image 14 to image 14, could be stored to track changes in slope from a positive trend (increasing mean intensity value 24) to a negative trend (decreasing mean intensity value 24). This is quite a common technique for detecting changes in polarity/direction/sign, etc.

According to another embodiment of a method according to the present invention an industry standard curve fitting algorithm (as is currently done, off-line/non-real-time, in quantification software such as the Philips QLAB ultrasound quantification software) is applied to determine the peak intensity as each image 14 arrives, in real-time. The curve fitting algorithms usually require mean intensity values and time vectors. Presumably, during the wash-in phase, the peak intensity frame 38 will change continuously until the wash-out phase when the mean intensity value 24 will start to decrease.

Since acquisition rates may vary for different transducers and system settings an alternative approach may be to compare images 14 over time. So, rather than determining a local average (over 3 subsequent images, for example) the mean intensity value would be averaged over 20 milliseconds for example.

According to yet another method "local" peaks are determined, in particular as an adaptation to an existing algorithm used in QLAB to determine peak frames in a subset. During wash-in, the general trend for mean echo intensity is to increase; however, in any subset of frames (3, 5, or 7 for example) the mean intensity value 24 may rise or fall from image 14 to image 14. By continually determining the local peaks and storing the results, a trend of the mean intensity value 24 can be stored and compared dynamically as each new image 14 arrives. When the trend is decreasing, it can be deduced that the wash-out phase 52 has begun.

The best (most accurate) approach will depend on image size, size of the region of interest 20, placement of the region of interest 20, and parameters used in the detection algorithms (as described above). It is envisioned that a combination of the previously described embodiments of the method may be employed to determine the peak intensity frame 38.

The display 26 can show the time to peak. The time to peak could either be computed as the time between the beginning of the acquisition of ultrasound images 14 and the detection of the peak 38 or, preferably, by showing the time between a start time that was indicated by the user and the time of the peak detection. For example, in this embodiment of the present invention the second user interface 32 comprises a button 34. By pressing the button 34 the user can indicate that the time to peak should be determined relative to the time of pushing the button. For example, the user could press the button when he administers the contrast agent into a patient. The administration of the contrast agent can be performed by injection or by swallowing or by inhalation. It can be performed either by a physician, a medical assistant, a person of ordinary skill or the patient himself. The button 34 of the second user interface 32 can also be pressed by the patient himself or by another person who is operating the ultrasound imaging system 10.

The transducer 12 acquires the ultrasound images 14 based on a number of acquisition parameters. The processor 28 is configured to change (S16) these parameters based on when it has detected a peak intensity. For example, it can reduce (S16) the storage frame rate at which the ultrasound images 14c are stored in storage 36 a few seconds after the peak 38 was detected (S14). The rate at which the transducer 12 acquires ultrasound images 14 is not necessarily identical to the rate at which images 14c are stored in the storage 36, the rate at which images 14a are shown on the display 18 of the first user interface 16 or the rate at which images 14b are used for computing (S12) a mean intensity value 24.

In a preferred embodiment, the rate at which the images 14 are acquired (S10) is identical to the rate at which images 14a, 14b are used for displaying and for determining a mean intensity value. The storage rate 46, 48, however, can be lower than the acquisition rate. In particular, a certain time, for example ten seconds, after the peak has been determined the storage rate can be reduced because it is assumed that these images are less informative about the imaged object.

The processor 28 can control the transducer 12 to reduce the storage frame rate once a certain time after the peak 38. For example, it could reduce the storage frame rate to half the acquisition rate ten seconds after the peak 38. In a preferred embodiment, the processor 28 continues to reduce the storage frame rate by increasing a decimation rate. For example, five seconds after the peak the storage frame rate could still be identical to the acquisition rate (decimation rate=1) but it could then be continuously reduced to 50% of the acquisition rate (decimation rate=2) at twenty seconds after the peak and down to 20% of the acquisition rate (decimation rate=5) at one minute after the peak.

During the wash-out period, the intensities keep decreasing and after some time the acquired images comprise no more additional useful information. The time until the wash-out of the contrast agent is completed depends, among other things, on the object that is being imaged. In one embodiment of the invention the second user interface 32 comprises a selection unit 35 that lets the user choose one of several objects, e.g. different organs such as liver, heart, gall bladder, etc. Depending on which object was chosen by the user, the processor 28 can control the transducer 12 to stop acquiring ultrasound images 14 a pre-determined time after the peak (this is not shown in the figures). For example, for liver imaging 90 seconds after the peak intensity is reached, typically there are no more relevant changes happening in the intensity in the region of interest 20. Hence, the processor 28 could stop the acquisition 90 seconds after the peak intensity. This further simplifies acquisition workflow (the user does not need to physically press a button to end image capture) and also ensures an optimized size of the files to be exported for post-acquisition analysis. The processor 28 can indicate the end of the image acquisition to the user by controlling loudspeaker 30 to generate an acoustic signal.

The storage 36 is not necessarily located in the same device as the reminder of the ultrasound imaging system. For example, the storage could be a network attached storage that is located in a separate room.

Figure 3:
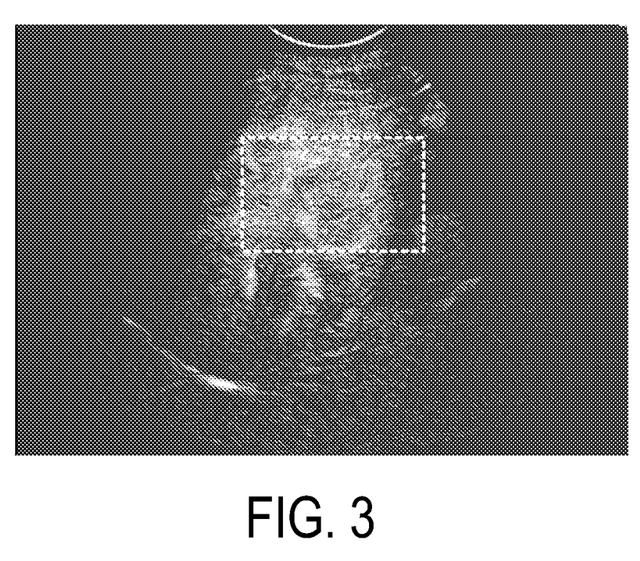
FIG. 3 and FIG. 4 show examples of ultrasound images and a region of interest defined in the images.
Figure 4:
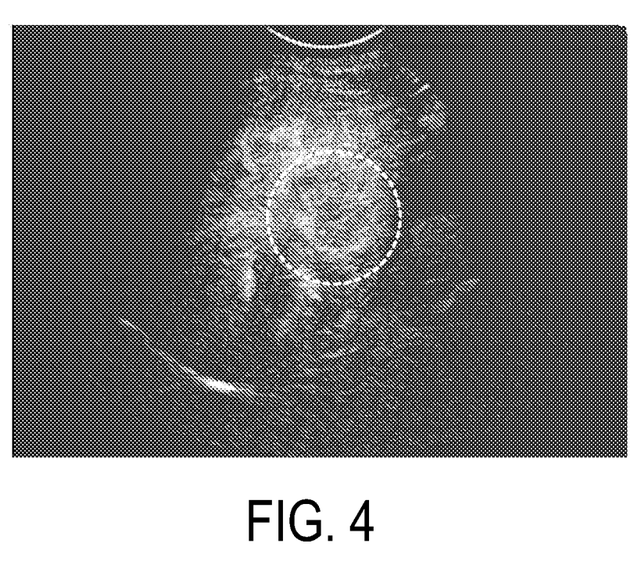

FIG. 3 and FIG. 4 show examples of ultrasound images 14 that are acquired with an ultrasound imaging system according to the present invention. FIG. 3 shows a rectangular region of interest 20, FIG. 4 shows a circular region of interest 20. Any other shape of the region 20 where the mean intensity values 24 are determined is also conceivable. In particular, the region 20 may also correspond to the complete ultrasound image 14.

Figure 5:
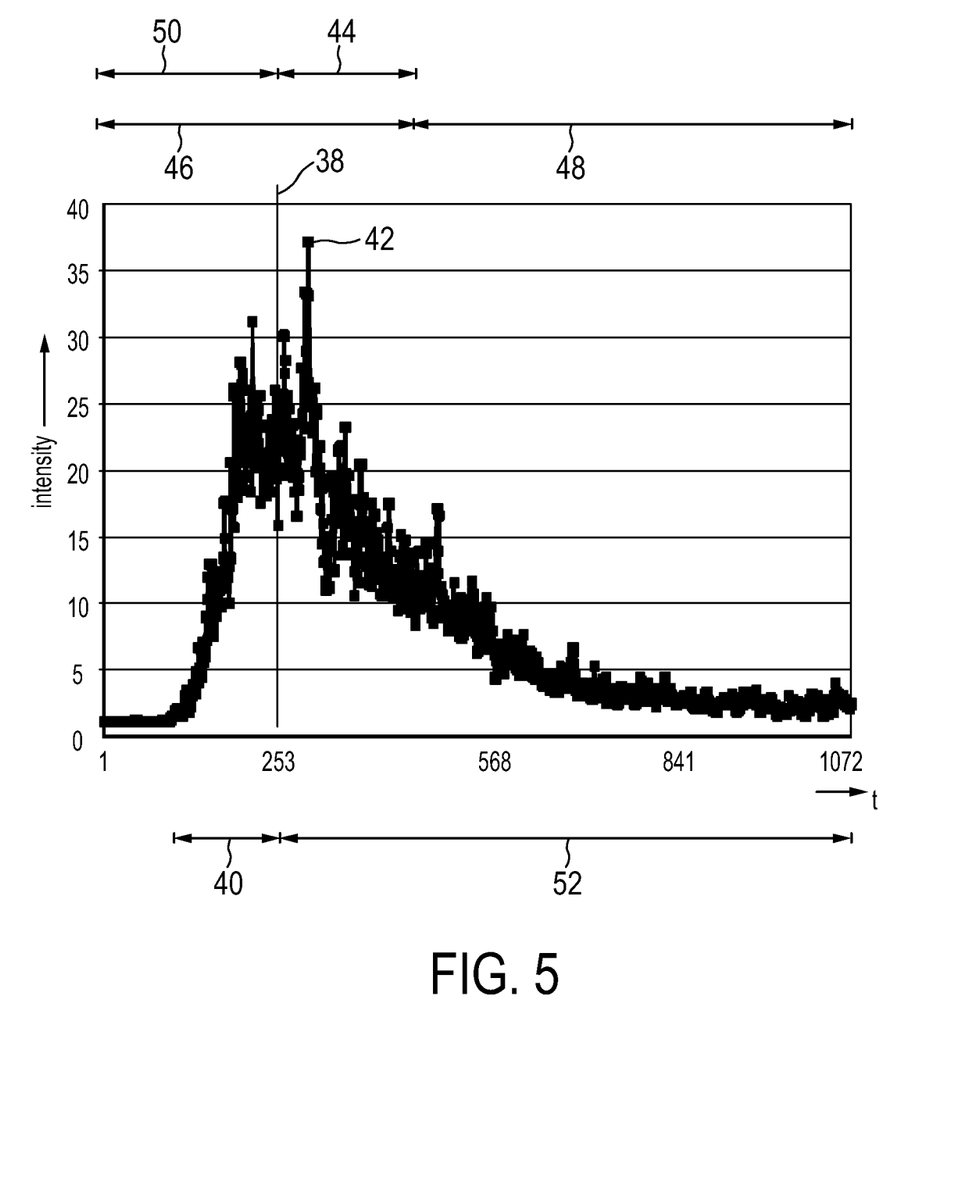
FIG. 5 shows an example of a time-intensity curve acquired with an ultrasound imaging system according to the present invention.

FIG. 5 shows an example of a time intensity curve that is obtained by plotting the mean intensity values of the subsequently acquired ultrasound images 14. The area from the beginning of intensity enhancement to the peak intensity frame 38 is called washed-in region 40. As can be seen in the plot, the peak intensity frame 38 does not necessarily correspond to the image 14 that has the highest mean intensity value in the region of interest 20. The maximum intensity frame 42 can occur at a different location than the peak intensity frame 38 either because the real time detection of the peak intensity was false or because the maximum intensity is caused by a local outlier. Because of noisy data it might be unclear where the true peak of the curve is located. In such cases an experienced physician might want to form his own opinion and it is important that the area around the assumed peak intensity frame 38 is acquired and stored with a high frame rate. From the beginning of the image acquisition until a predetermined time 44 after the peak intensity frame 38 the ultrasound images 14 are acquired with a high storage frame rate 46. Afterwards the images are still acquired at the same acquisition frame rate but stored in the storage at a reduced storage frame rate 48.

Once the processor has determined the peak intensity frame 38, the processor 28 can control the display 26 to show the time to peak 50 and the wash-in time 40. In one embodiment of the present invention, the processor 28 determines a second peak intensity frame 38 also after it has already determined a first peak intensity frame. This way, if an image has been falsely identified as peak intensity frame 38, the processor can determine a second peak intensity frame 38, which is then assumed to be the true peak intensity frame 38. In this case the display values of time to peak 50 and wash-in time 40 on the display 26 are updated.

The period after the peak intensity 38 is called wash-out region 52. During the wash-out region the mean intensity values 24 decrease as the contrast agent is washed-out from the object. The processor 28 can control the transducer 12 to stop the acquisition of ultrasound images 14 either when the mean intensity values 24 are below a predefined threshold or, as previously described, when an object-dependent predetermined time after the acquisition of the peak intensity frame 38 has passed.

In summary, the proposed invention allows real-time detection of a peak of mean intensity in an ultrasound image and changing of an acquisition parameter once a peak has been determined. The acquisition parameter that is changed after peak detection depends on the concrete application. In the case of contrast-enhanced ultrasound imaging where a contrast agent is administered into a patient, the acquisition parameter storage frame rate can be reduced after detection of a peak of mean intensity. However, there are also applications possible, e.g. in the absence of any contrast agent, the mean intensities could increase when some part of an organ of a person has moved into the field of view of the ultrasound device. In this case, an acquisition and storage frame rate could be increased after a detection of a peak of mean intensities. Other acquisition parameters that could be changed based on a peak intensity detection include, but are not limited to, depth of an image, the location of the transmit focus, the number of focal zones, whether to use the B mode or color Doppler mode, and whether harmonic or fundamental frequencies are to be used for imaging.

While the invention has been illustrated and described in detail in the drawings and foregoing description, such illustration and description are to be considered illustrative or exemplary and not restrictive; the invention is not limited to the disclosed embodiments. Other variations to the disclosed embodiments can be understood and effected by those skilled in the art in practicing the claimed invention, from a study of the drawings, the disclosure, and the appended claims.

In the claims, the word "comprising" does not exclude other elements or steps, and the indefinite article "a" or "an" does not exclude a plurality. A single element or other unit may fulfill the functions of several items recited in the claims. The mere fact that certain measures are recited in mutually different dependent claims does not indicate that a combination of these measures cannot be used to advantage.

A computer program may be stored/distributed on a suitable non-transitory medium, such as an optical storage medium or a solid-state medium supplied together with or as part of other hardware, but may also be distributed in other forms, such as via the Internet or other wired or wireless telecommunication systems.

Any reference signs in the claims should not be construed as limiting the scope.

The invention claimed is:

1. An ultrasound imaging system comprising:
a transducer configured to acquire ultrasound images of an object based on one or more adjustable acquisition parameters,
a storage configured to store the ultrasound images,
an analyzer configured to analyze an ultrasound image in real-time for a mean intensity value, and a processor configured to determine in real-time when the mean intensity value has reached a peak
characterized in that
the adjustable acquisition parameters comprise a storage frame rate at which the transducer stores ultrasound images in the storage,
and in that the processor is configured to reduce the storage frame rate after a peak has been determined.

2. The ultrasound imaging system according to claim 1, wherein the processor is configured to compare the mean intensity value of a current image with the mean intensity values of one or more previous images for determining when the mean intensity value has reached a peak.

3. The ultrasound imaging system according to claim 1, further comprising a notification unit, in particular an LED, a display, or a loudspeaker, wherein the processor is configured to control the notification unit to notify a user when it has determined that the mean intensity value has reached a peak.

4. The ultrasound imaging system according to claim 1, wherein the processor is configured to continuously reduce the storage frame rate after it has determined that the mean intensity value has reached a peak.

5. The ultrasound imaging system according to claim 1, wherein the processor is further configured to control the transducer to stop acquiring ultrasound images a predetermined time after it has determined that the mean intensity has reached a peak.

6. The ultrasound imaging system according to claim 5, further comprising a first user interface for identifying the object as one of several objects, wherein the predetermined time depends on the selected object.

7. The ultrasound imaging system according to claim 1, wherein the mean intensity value is the mean intensity of a region of interest within the ultrasound images.

8. The ultrasound imaging system according to claim 1, wherein the analyzer is further configured to analyze the ultrasound image for a time to peak, a transit time, a wash-in time and/or a wash-out time.

9. Method for acquiring and analyzing ultrasound images comprising the steps of:
acquiring ultrasound images of an object based on one or more acquisition parameters, said acquisition parameters comprising a storage frame rate at which the acquired ultrasound images are stored in a storage,
analyzing an ultrasound image in real-time for a mean intensity value,
determining when the mean intensity value has reached a peak,
and changing at least the storage frame rate after a peak has been determined such that the storage frame rate is reduced.

10. Computer program comprising a non-transitory computer readable medium including a computer program code means for causing a computer, when said computer program is carried out on the computer, to carry out the steps of:
analyzing an ultrasound image in real-time for a mean intensity value, said ultrasound image being one of a plurality of ultrasound images of an object acquired based on one or more acquisition parameters, said acquisition parameters comprising a storage frame rate at which the acquired ultrasound images are stored in a storage,
determining when the mean intensity value has reached a peak, and
changing at least the storage frame rate after a peak has been determined such that the storage frame rate is reduced.

* * * * *